United States Patent [19]

Harrison et al.

[11] Patent Number: 5,559,121
[45] Date of Patent: Sep. 24, 1996

[54] RAPAMYCIN FORMULATIONS FOR ORAL ADMINISTRATION

[75] Inventors: Maureen M. Harrison, St. Albans, Vt.; Christian L. Ofslager, Plattsburgh; Robert P. Waranis, Chazy, both of N.Y.; Thomas W. Leonard, Wilmington, N.C.

[73] Assignee: American Home Products Corporation, Madison, N.J.

[21] Appl. No.: 448,280

[22] Filed: May 23, 1995

Related U.S. Application Data

[63] Continuation-in-part of Ser. No. 129,523, Sep. 30, 1993, abandoned.

[51] Int. Cl.$^6$ .......................... A61K 31/33; A61K 31/71
[52] U.S. Cl. ........................................................ 514/291
[58] Field of Search ................................................ 514/291

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,885,171 | 12/1989 | Surendra et al. | 424/122 |
| 5,080,899 | 1/1992 | Sturm et al. | 514/291 |
| 5,100,899 | 3/1992 | Caln | 514/291 |

FOREIGN PATENT DOCUMENTS

| | | |
|---|---|---|
| 0041795 | 12/1981 | European Pat. Off. . |
| 0428162 | 5/1991 | European Pat. Off. . |
| 0444659 | 9/1991 | European Pat. Off. . |

OTHER PUBLICATIONS

Physicians' Desk Reference, 45th ed., 1991, pp. 2119–2122, Medical Economics Company, Inc.
Physicians' Desk Reference, 45th ed., 1991, pp. 785–787, Medical Economics Company, Inc.
Luke et al., Effects of Cyclosporine on the Isolated Perfused Rat Kidney, Transplantation, vol. 43, No. 6, pp. 795–799, 1987.
Venkataram, et al., Pharmacokinetics of Two Alternative Dosage Forms for Cyclosporine: Liposomes and Intralipid, Journal of Pharmaceutical Sciences, vol. 79, No. 3, pp. 216–219, 1990.
Thiel, et al., Acutely Impaired Renal Function During Intravenous Administration of Cyclosporine A: A Cremaphore Side–Effect, Clinical Nephrology, vol. 25, Suppl. No. 1., pp. S40–42, 1986.
Honbo, et al., The Oral Dosage Form of FK–506, Transplanation Proceedings, vol. XIX, No. 5, Suppl. 6, pp. 17–22, 1987;.
Stepkowski, et al., Rapamycin, A Potent Immunosuppressive Drug for Vascularized Heart, Kidney, and Small Bowel Transplantation in the Rat, Transplantation, vol. 51, No. 1, pp. 22–24, 1991.
Kahan, et al., Synergistic Interactions of Cyclosporine and Rapamycin to Inhibit Immune Performances of Normal Human Peripheral Blood Lymphocytes In Vitro, Transplantation, vol. 51, No. 1, pp. 232–237, 1991.
Intl. Pharm. Abstracts—FK–506, Immunosuppressant for the 1990s, Macleod, et al., Lancet, 337, pp. 25–27, Jan. 5, 1991.
Intl. Pharm. Abstracts, FK–506: Discussion of a New Investigationsl Drug, C. G. Forde, ASHP Midyear Clinical Meeting, 25, p. 446D, Dec. 1990.
Intl. Pharm. Abstracts, FK–506, Kidney Transplantation Under FK 506, Starzl, et al., JAMA, 264, pp. 63–67, Jul. 4, 1990.
Intl. Pharm. Abstracts—FK–506 In Steroid–Resistant Focal Sclerosing Glomerulonephritis of Childhood, McCauley, et al., Lancet, 335, p. 674, Mar. 17, 1990.
Intl. Pharm. Abstracts, New Drug Could Replace Cyclosporin in Transplant Drug Therapy, Anon, Am. Pharm. NS, 30, 16, Jan. 1990.
Intl. Pharm. Abstracts, Treatment of Cyclosporin Induced Hemolytic–Uremic Syndrome with FK–506, McCauley, et al., Lancet, 2, 1516, Dec. 23–30, 1989.
Intl. Pharm. Abstracts—FK–506 for Liver, Kidney, and Pancreas Transplantation; Starzl, et al., Lancet, 2, 1000–1004, Oct. 28, 1989.
The Merck Index, Ninth Ed., pp. 5287–5288, 1976.

*Primary Examiner*—Phyllis G. Spivack
*Attorney, Agent, or Firm*—Steven R. Eck

[57] ABSTRACT

The present invention comprises oral rapamycin formulations which contain, per 100 ml of the formulation, from about 0.01 to about 10.0 grams per 100 ml of rapamycin, from about 0.1 to about 10 ml of surfactant, from about 0.1 to about 25 ml of N,N-dimethylacetamide, and from about 65 to about 99.8 ml of a lecithin or phospholipid solution.

10 Claims, No Drawings

RAPAMYCIN FORMULATIONS FOR ORAL ADMINISTRATION

RELATED APPLICATIONS

This is a continuation-in-part of application Ser. No. 08/129,523, filed Sep. 30, 1993, now abandoned.

This invention relates to formulations containing rapamycin, or pharmaceutically acceptable salts of rapamycin, which are useful in oral administrations for inducing immunosuppression and for treating transplantation rejection, host vs. graft disease, autoimmune diseases, diseases of inflammation, solid tumors, fungal infections, adult T-cell leukemia/lymphomas and hyperproliferative vascular disorders.

BACKGROUND OF THE INVENTION

Rapamycin is a macrolide antibiotic produced by *Streptomyces hygroscopicus* which was discovered first for its properties as an antifungal agent. It adversely affects the growth of fungi such as *Candida albicans* and *Microsporum gypseum*. Rapamycin, its preparation and its antibiotic activity were described in U.S. Pat. No. 3,929,992, issued Dec. 30, 1975 to Surendra Sehgal et al. In 1977 Martel, R. R. et al. reported on immunosuppressive properties of rapamycin against experimental allergic encephalitis and adjuvant arthritis in the Canadian Journal of Physiological Pharmacology, 55, 48–51 (1977). In 1989, Calne, R. Y. et al. in Lancet, 1989, no. 2, p. 227 and Morris, R. E. and Meiser, B. M. in Medicinal Science Research, 1989, No. 17, P. 609–10, separately reported on the effectiveness of rapamycin in inhibiting rejection in vivo in allograft transplantation. Numerous articles have followed describing the immunosuppressive and rejection inhibiting properties of rapamycin, and clinical investigations have begun for the use of rapamycin in inhibiting rejection in transplantation in man.

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], and smooth muscle cell proliferation and intimal thickening following vascular injury [Morris, R. J. Heart Lung Transplant 11 (pt. 2): 197 (1992)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42- positions. U.S. Pat. No. 5,118,678 discloses carbamates of rapamycin that are useful as immunosuppressive, anti-inflammatory, antifungal, and antitumor agents. U.S. Pat. No. 5,100,883 discloses fluorinated esters of rapamycin. U.S. Pat. No. 5,118,677 discloses amide esters of rapamycin. U.S. Pat. No. 5,130,307 discloses aminoesters of rapamycin. U.S. Pat. No. 5,117,203 discloses sulfonates and sulfamates of rapamycin. U.S. Pat. No. 5,194,447 discloses sulfonylcarbamates of rapamycin.

U.S. Pat. No. 5,100,899 (Calne) discloses methods of inhibiting transplant rejection in mammals using rapamycin and derivatives and prodrugs thereof. Other chemotherapeutic agents listed for use with rapamycin are azathioprine, corticosteroids, cyclosporin (and cyclosporin A), and FK-506, or any combination thereof.

The primary immunosuppressive agent presently used for inhibiting rejection in the allograft transplantation of organs in man is cyclosporine (Sandimmune®). Cyclosporine is a cyclic polypeptide consisting of 11 amino acids. The intravenous injectable formulation of Sandimmune® (IV) is a sterile ampul containing, per ml, 50 mg of cyclosporine, 650 mg of Cremophor® EL and alcohol Ph Helv. (32.9% by volume) (under nitrogen). For administration this mixture is diluted further with 0.9% Sodium Chloride Injection or 5% Dextrose Injection before use. (*Physicians' Desk Reference*, 45th ed., 1991, pp. 1962–64, Medical Economics Company, Inc.) The macrolide molecule designated FK506, which has certain structural similarities to rapamycin, is also currently undergoing clinical investigation for inhibiting rejection in allograft organ transplantation in man. FK506 is isolated from *Streptomyces tsuskubaensis* and is described in U.S. Pat. No. 4,894,366 to Okuhara et al., issued Jan. 16, 1990 R. Venkataramanan et al., in Transplantation Proceedings, 22, No. 1, Suppl., 1 pp 52–56 (February 1990), report that the intravenous injectable formulation of FK506 is provided as a 10 mg/ml solution of FK506 in polyoxyethylated castor oil (HCO-60, a surfactant) and alcohol. The intravenous preparation must be diluted with saline or dextrose and administered as an infusion for 1 to 2 hours.

The *Physicians' Desk Reference* (45th ed., 1991, p. 2119, Medical Economics Company, Inc.) lists cyclosporine under the Sandimmune® tradename as available in 25 mg and 100 mg strength capsules and as an oral solution in 50 ml bottles. The 25 mg capsules contain 25 mg cyclosporine, USP, and alcohol, USP dehydrated, at a maximum of 12.7% by volume. The 100 mg capsules contain cyclosporine, USP, 100 mg and alcohol, USP dehydrated, at a maximum 12.7% by volume. Inactive ingredients in the oral capsules are corn oil, gelatin, glycerol, Labrafil M 2125 CS (polyoxyethylated glycolysed glycerides), red iron oxide, sorbitol, titanium dioxide, and other ingredients. The oral solution is available in 50 mg bottles containing cyclosporine, USP, 100 mg and Ph. Helv. alcohol at 12.5% by volume dissolved in olive oil, Ph. Helv./Labrafil M 1944 CS (polyoxyethylated oleic glycerides) vehicle which must be diluted further with milk, chocolate milk or orange juice before oral administration.

Azathioprine (available from Burroughs Wellcome Co., Research Triangle Park, N.C., under the tradename Imuran®) is another orally administered immunosuppressive agent prescribed alone or in conjunction with other immunosuppressive agents. The *Physicians' Desk Reference* (45th ed., 1991, pp. 785–787, Medical Economics Company, Inc.) lists azathioprine as 6-[1-methyl-4-nitroimidazol- 5-yl)thio] purine, which is provided for oral administration in scored tablets containing 50 mg azathioprine and the inactive ingredients lactose, magnesium stearate, potato starch, povidone, and stearic acid.

DESCRIPTION OF THE INVENTION

Methods of drug delivery are designed to deliver an acceptable dosage of the medication to the patient. In the case of oral formulations, it is highly desirable to provide a dosage form which meets this criteria and which can be effectively administered, preferably self-administered, in either clinical or non-clinical situations. The present invention concerns formulations useful in the oral administration of rapamycin. Rapamycin has been shown to possess immunosuppressive, antifungal and antiinflammatory activity in vivo and to inhibit thymocyte proliferation in vitro. Therefore, these formulations are useful in the treatment of Candida albicans infections, diseases of inflammation and transplant rejection autoimmune diseases, including lupus, rheumatoid arthritis, diabetes melitus, multiple sclerosis, etc.

Because the formulations disclosed herein contain rapamycin, they are considered to have antitumor, antifungal and antiproliferative activities. As such, the formulations of this invention are useful in the treatment of transplantation rejection, such as heart, kidney, liver, bone marrow and skin transplants; autoimmune diseases such as lupus, rheumatoid arthritis, diabetes mellitus, myasthenia gravis and multiple sclerosis; diseases of inflammation such as psoriasis, dermatitis, eczema, seborrhea, inflammatory bowel disease and eye uveitis; solid tumors; fungal infections; and hyperproliferative vascular diseases, such as restenosis. The present invention, therefore, also provides formulations useful for inducing immunosuppression in a mammal in such need. Such inducements would comprise administering to said mammal an immunosuppressive amount of one or more of the formulations discussed herein.

As rapamycin has been found to have poor water and oil solubility, the present formulations consist of a rapamycin solution containing an organic solvent and lecithin. In general, the formulations of this invention concern combinations of a) rapamycin, b) surfactant, c) N,N-dimethylacetamide (DMA) and d) lecithin or phospholipid in the following ranges (per 100 ml formulation):

a) rapamycin at a concentration of from about 0.01 to about 10.0 grams per 100 ml;

b) surfactant at a concentration of from about 0.1 to about 10.0 ml per 100 ml;

c) DMA at a concentration of from about 0.1 to about 25 ml per 100 ml; and d) from about 65 to about 99.8 ml per 100 ml of a lecithin or phospholipid solution containing from 40 to 60 percent lecithin or phospholipid in suitable solvent.

More preferred formulations of the present invention include those combinations having the following ranges of materials:

a) rapamycin at a concentration of from about 0.05 to about 5.0 grams per 100 ml;

b) surfactant at a concentration of from about 0.5 to about 8.0 ml per 100 ml;

c) DMA at a concentration of from about 0.5 to about 20 ml per 100 ml; and d) from about 72 to about 99.0 ml per 100 ml of a lecithin or phospholipid solution containing from 40 to 60 percent lecithin or phospholipid in suitable solvent.

The most preferred formulations of this invention include those having the following ranges of concentrations:

a) rapamycin at a concentration of from about 0.10 to about 1.0 gram per 100 ml;

b) surfactant at a concentration of from about 1.0 to about 5.0 ml per 100 ml;

c) DMA at a concentration of from about 1.0 to about 10 ml per 100 ml; and d) from about 85 to about 98 ml per 100 ml of a lecithin or phospholipid solution containing from 40 to 60 percent lecithin or phospholipid in suitable solvent.

The examples provided below list a number of solvents that are useful in the formulations of the present invention. Alternate solvents that can be used include, but are not limited to, dimethylacetamide, ethanol, dimethylformamide, t-butanol and propylene glycol. The amounts of the solvents can be raised in conjunction with the drug concentration(s). As another alternative, the amounts of the solvents can be reduced in conjunction with the drug concentration and, if drug solubility permits, the lecithin alone can act as the solvent.

Surfactants that may be used with the present formulations include, but are not limited to, Polysorbate 20 (polyoxyethylene 20 sorbitan monolaurate), Polysorbate 60, Span 80® Sorbitan Oleate, a product of ICI Americas, Wilmington, Del., the Cremophor® surfactants produced by the BASF Corporation, Parsippany, N.J., and Polysorbate 80, which is defined by the Merck Index, 11th Edition, published by Merck & Co., Inc., Copyright 1989, on page 1254 as Sorbitan mono-9-octadecenoate poly(oxy-1,2-ethanediyl) derivatives, polyoxyethylene (20) sorbitan mono-oleate, Sorbitan mono-oleate polyoxyethylene, Sorlate, Tween 80, among others, and indicates an oleate ester of sorbitol and its anhydrides copolymerized with approximately 20 moles of ethylene oxide for each mole of sorbitol and sorbitol anhydrides. Polysorbate 80 is the surfactant preferred with the present invention.

A number of lecithin or phospholipid solutions may be used in the present formulations. Lecithin is a general term for phosphatidylcholine or a mixture of various diglycerides of stearic, palmitic, and oleic acids, linked to the choline ester of phosphoric acid. Various types of lecithin or lecithin sourced products (such as separated phospholipids), either alone or mixed with various solvents, can be used as the final ingredient of the formulations mentioned above. These lecithin ingredients can include, for example, Alcolec® lecithin, produced by the American Lecithin Company, Danbury, Conn., Phosal 50 PG propylene glycol and lecithin, Phosal 50 MCT phosphatidylcholine and medium chained triglycerides, and Phospholipan 90® lecithin, all of which are produced by Nattermann Phospholipid GMBH, Colone, Germany, the Centrophil® and Centrophase® lecithins produced by Central Soya, Fort Wayne, Ind. It is preferred that the phospholipid solutions used in the present formulation have at least a 50% concentration of phospholipid. More particularly, it is preferred that the lecithin products or solutions used with the present formulations have at least 50% phosphatidylcholine. It is also preferred that the phospholipid solution comprise a phospholipid in propylene glycol.

The dosage requirements may vary the severity of the symptoms presented and the particular subject being treated. Projected daily oral dosages of the compounds of this invention would be 0.005–75 mg/kg, preferably between 0.01–50 mg/kg, and more preferably between 0.05–10 mg/kg.

Treatment will generally be initiated with small dosages less than the optimum dose of the compound. Thereafter the dosage is increased until the optimum effect under the circumstances is reached. Precise dosages will be determined by the administering physician based on experience with the individual subject treated. In general, the formulations of this invention are most desirably administered at a concentration that will generally afford effective results without causing any harmful or deleterious side effects.

The present formulations may be administered to the patient by the means generally used for oral liquid medications. They may be taken, by themselves, or they may be dispersed in a liquid, such as water or juices. The formulations may also be capsulized, such as in starch capsules or soft elastic gelatin capsules. Rapamycin oral may be dispersed into water for dosing in the range of about 1 part of formula into about 9 parts water downward to about 1 part of formula into about 499 parts water by mixing for a minimum of about 60 seconds. This dispersion may be used over about a 1 hour period with mixing prior to dosing.

It is contemplated that when the formulations of this invention are used as an immunosuppressive or antiinflammatory agent, they can be administered in conjunction with one or more other immunoregulatory agents. Such other antirejection chemotherapeutic agents include, but are not limited to azathioprine, corticosteroids, such as prednisone and methylprednisolone, cyclophosphamide, cyclosporin A, FK- 506, OKT-3, and ATG. By combining one or more of the formulations of the present invention with such other drugs or agents for inducing immunosuppression or treating inflammatory conditions, lesser amounts of each of the agents may be required to achieve the desired effect. The basis for such combinatin therapy was established by Stepkowski whose results showed that the use of a combination of rapamycin and cyclosporin A at subtherapeutic doses significantly prolonged heart allograft survival time. [Transplantation Proc. 23:507 (1991)].

It is also understood that the present formulations may be used with other ingredients used with conventional oral formulations such as, but not limited to, flavor enhancers, coloring agents, adjuvants, antifungal agents, antibacterial agents, etc.

The following non-limiting examples and comparative examples are provided to illustrate the effectiveness of the more preferred embodiments of the present invention.

EXAMPLES

Example 1

The following Example 1 demonstrates an oral rapamycin formulation having a concentration of rapamycin which is 50 mg/ml.

A. Formula:

| Ingredients | Amount |
| --- | --- |
| Rapamycin @ 100% | up to 5.0 gm |
| Polysorbate 80, NF | 5.0 ml or 5.4 gm |
| N,N-dimethylacetamide | 20.0 ml or 18.7 gm |
| Phosal 50 PG[1] | q.s. 100 ml or 99.6 gm |

[1]Nattermann brand of lecithin and propylene glycol

Manufacturing Directions:

1. Weigh the rapamycin into a suitable container.
2. Add the N,N-dimethylacetamide to the container in Step #1. Mix until dissolved.
3. Add the Polysorbate 80 to the container in Step #2. Mix until uniform.

4. Adjust to the final volume with Phosal 50 PG® lecithin and propylene glycol.
5. Mix until uniform Two Cynomolgus monkeys, listed below as A and B, were administered the above formulation at a dose of 50 mg/kg of rapamycin and the following serum concentrations were determined at the indicated time after dosing.

| Rapamycin Concentration in Monkey Serum Dosed Orally with 50 mg/kg | | |
| --- | --- | --- |
| Time | A | B |
| 0 | BDL | BDL |
| 1 hr | 0.017 | 0.035 |
| 2 hr | 0.037 | 0.166 |
| 3 hr | 0.062 | 0.078 |
| 4 hr | 0.215 | 0.115 |
| 6 hr | 0.262 | 0.050 |
| 9 hr | 0.103 | 0.010 |
| 12 hr | 0.018 | BDL |

BDL = Below detection limit (detection limit ~ or equal to 0.006 μg/ml)

Example 2

The following Example 2 provides a oral formulation having a rapamycin concentration of 125 mg/ml, as well as the procedure for its preparation. The first set of ingredients and procedures provided demonstrate the production of an oral rapamycin concentrate. The second set of ingredients and procedures provided demonstrate a diluent which may be used with the rapamycin concentrate.

Rapamycin Oral Concentration at 125 mg/ml in DMA

Formula:

| Ingredients | Amount |
| --- | --- |
| Rapamycin @ 100% | 12.5 gm |
| Dimethylacetamide (DMA) | q.s. 100 ml |

Procedure:

1. Weigh 12.5 g of rapamycin into a suitably calibrated container.
2. Q.S. to 100 ml with DMA.
3. Mix until a clear solution is formed.
4. Store rapamycin concentrate in all glass container or in a flint glass vial stoppered with a Teflon barrier faced stopper.

The following Diluent No. 1 is used in the oral rapamycin formula (rapamycin at 25 mg/ml) which follows:

Diluent No. 1 for Oral Rapamycin

Formula:

| Ingredients | Amount |
| --- | --- |
| Polysorbate 80 | 6.69 gm |
| Centrophil W[1] | q.s. 100 ml |

[1]Central Soya brand of lecithin

Procedure:

1. Add 6.69 grams of Polysorbate 80 to a suitable container

2. Q.S. to 100 ml with Centrophil W® lecithin.

3. Mix until homogeneous.

4. Diluent for oral rapamycin can be stored in an all glass container or in a flint glass vial stoppered with a Teflon barrier faced stopper at room temperature.

Rapamycin Oral at 25 mg/ml

Formula:

| Ingredients | Amount |
| --- | --- |
| Rapamycin Oral Concentrate @ 125 mg/ml | 20 ml |
| Diluent for Oral Rapamycin | q.s. 100 ml |

Procedure:

1. Place 20 ml of rapamycin oral concentrate into a container.

2. Q.S. to 100 ml with diluent for oral rapamycin.

3. Mix until homogeneous.

4. This rapamycin formula can be stored in an all glass container or in a flint glass vial stoppered with a Teflon barrier faced stopper.

Four Cynomolgus monkeys, listed below as A–D, were administered the above formulation at a dose of 50 mg/kg of rapamycin and the following serum concentrations were determined at the indicated time after dosing.

Rapamycin Concentration in Monkey Serum Dosed Orally with 50 mg/kg

| | Rapamycin Concentration (μg/ml) Monkey No. | | | |
| --- | --- | --- | --- | --- |
| Time | A | B | C | D |
| 0 | BDL | BDL | BDL | BDL |
| 1 hr | 0.008 | 0.786 | 0.078 | 0.053 |
| 2 hr | 0.020 | 0.129 | 0.066 | 0.013 |
| 3 hr | 0.026 | 0.077 | 0.101 | 0.022 |
| 4 hr | 0.104 | 0.036 | >0.200 | 0.057 |
| 6 hr | QNS | 0.029 | >0.200 | 0.117 |
| 9 hr | 0.113 | 0.012 | >0.200 | 0.031 |
| 12 hr | 0.022 | 0.005 | 0.050 | 0.005 |

QNS = Quantity not sufficient.
BDL = Below detection limit (detection limit ~ or equal to μg/ml)

COMPARATIVE EXAMPLES

Comparative Example 1

The following traditional formulation approaches applied to rapamycin are provided as a comparison to those of the present invention. The ingredients and manufacturing directions for Diluent No. 2, below, are used to create the diluent in the comparative oral formulation (Rapamycin Oral Suspension at 50 mg/ml) which follows:

| Diluent for Rapamycin Suspension | |
| --- | --- |
| Ingredients | Amount |
| Polysorbate 80, NF | 5.0 ml |
| 0.5 M Citric Acid (pH 4) | q.s. 100 ml |

Manufacturing Directions:

1. Prepare a 0.5M citric acid solution.

2. Adjust the pH of the solution in Step #1 to 4.0 using 50% w/w NaOH.

3. Place the Polysorbate 80 into a suitable container.

4. QS to 100 ml with solution from step #2.

5. Mix until uniform.

Rapamycin Oral Suspension at 50 mg/ml

| Ingredients | Amount |
| --- | --- |
| Rapamycin Micronized @ 100% | up to 5.0 gm |
| Diluent for Rapamycin Oral Suspension | q.s. 100 ml |

Manufacturing Directions:

1. Weigh the rapamycin into a suitable container.

2. QS with the diluent for rapamycin

3. Mix until uniform.

Three Cynomolgus monkeys, listed below as A–C, were administered the above formulation at a dose of 50 mg/kg of rapamycin and the following serum concentrations were determined at the indicated time after dosing.

Rapamycin Concentration in Monkey Serum Dosed Orally with 50 mg/kg Rapamycin Oral Suspension

| | Rapamycin Concentration (μg/ml) Monkey No. | | |
| --- | --- | --- | --- |
| Time | A | B | C |
| 0 | BDL | BDL | BDL |
| 1 hr | BDL | BDL | BDL |
| 2 hr | BDL | BDL | BDL |
| 3 hr | BDL | BDL | BDL |
| 4 hr | BDL | BDL | BDL |
| 6 hr | BDL | BDL | BDL |
| 9 hr | BDL | BDL | BDL |
| 12 hr | BDL | BDL | BDL |

BDL = Below detection limit (detection limit ~ or equal to 0.006 μg/ml).

Comparative Example 2

The following ingredients and procedural steps demonstrate the production of another traditional approach which has been applied to form an oral rapamycin solution, which is provided for comparison with the present invention.

Rapamycin Oral Solution at 50 mg/ml

Formula:

| Ingredients | Amount |
| --- | --- |
| Rapamycin @ 100% | 5.0 gm |
| Dimethylacetamide | 10.0 gm |
| Absolute Ethanol | 10.0 gm |
| Miglyol 812 | q.s. 100 ml |

Procedure:

1. Place rapamycin into a suitable container.

2. Add the dimethylacetamide and ethanol to the container in Step #1 and mix until a solution results.

3. QS with Miglyol 812 and mix until uniform.

4. (Alternative Step) Filter sample through a 0.2 micron Teflon filter.

Three Cynomolgus monkeys, listed below as A–C, were administered the above formulation at a dose of 50 mg/kg of rapamycin and the following serum concentrations were determined at the indicated time after dosing.

| Rapamycin Concentration in Monkey Serum Dosed Orally with 50 mg/kg Rapamycin Oral Suspension | | | |
|---|---|---|---|
| | Rapamycin Concentration (µg/ml) Monkey No. | | |
| Time | A | B | C |
| 0 | BDL | BDL | BDL |
| 1 hr | BDL | BDL | BDL |
| 2 hr | BDL | BDL | BDL |
| 3 hr | BDL | BDL | BDL |
| 4 hr | BDL | BDL | BDL |
| 6 hr | BDL | BDL | BDL |
| 9 hr | BDL | BDL | BDL |
| 12 hr | BDL | BDL | BDL |

BDL = Below detection limit (detection limit ~ or equal to 0.006 µg/ml).

Comparative Example 3

Rapamycin Oral Emulsion at 50 mg/ml

Formula:

| Ingredients | Amount |
|---|---|
| Rapamycin @ 100% | 5.0 gm |
| Dimethylacetamide | 10 ml |
| Olive Oil | q.s. 100 ml |

Procedure:

1. Place the rapamycin into a suitable container.

2. Add the dimethylacetamide to the container in Step #1 and mix until clear.

3. QS with olive oil and mix until homogenous.

Three Cynomolgus monkeys, listed below as A–C, were administered the above formulation at a dose of 50 mg/kg of rapamycin and the following serum concentrations were determined at the indicated time after dosing.

| Rapamycin Concentration in Monkey Serum Dosed Orally with 50 mg/kg Rapamycin Oral Emulsion | | | |
|---|---|---|---|
| | Rapamycin Concentration (µg/ml) | | |
| Time | A | B | C |
| 0 | BDL | BDL | BDL |
| 20 min | BDL | BDL | BDL |
| 40 min | BDL | BDL | BDL |
| 80 min | BDL | BDL | BDL |
| 3 hr | BDL | BDL | BDL |
| 6 hr | BDL | 0.110* | BDL |
| 12 hr | BDL | BDL | BDL |
| 24 hr | BDL | BDL | BDL |

BDL = Below detection limit (detection limit ~ or equal to 0.006 µg/ml).
*assay result obtained from test lab appears aberent.

Comparative Example 4

The oral rapamycin formulation seen as Example 1 was produced by the method disclosed, above, and is referred to in this example as Formula I.

An additional rapamycin formulation, Comparative Formula 4, for oral administration was produced by a method which comprises adding rapamycin to the DMA and mixing until a solution results, adding the listed amount of Polysorbate 80 to this mixture with mixing until clear and then bringing the sample to volume with polyethylene glycol (PEG) 400 and mixing until uniform. The sample of Comparative Formula 4 was then filtered to remove particulates, packaged, and stored refrigerated and protected from light.

Comparative Formula 4

| Ingredients | Amount |
|---|---|
| Rapamycin @ 100% | 5.0 gm |
| N,N-dimethylacetamide | 20.0 ml or 18.7 gm |
| Polysorbate 80, NF | 10.0 ml or 10.8 gm |
| Polyethylene Glycol 400, NF qs | 100 ml |

Manufacturing Directions:—One Component

1. Weigh rapamycin into a suitable container.

2. Add the N,N-dimethylacetamide to the container in Step #1. Mix until a solution results.

3. Add the Polysorbate 80 to the solution in Step #2. Mix until uniform.

4. QS to 100 ml with Polyethylene Glycol (PEG) 400. Mix sample until uniform.

5. Sterile filter sample through a 0.2 micron polytetrafluoroethylene (PTFE) filter.

6. Store sample refrigerated and protected from light.

Comparative Testing

Six Cynomolgus monkeys, listed in the table, below, as A through F, were at separate times administered the above formulations at a dose of 50 mg/kg of rapamycin. The monkeys' serum concentrations of rapamycin were determined at various time points to generate plots of rapamycin serum concentrations versus time. The area under the curve (AUC) from these oral dosings were compared to the AUC resulting from IV dosing of rapamycin to determine the absolute bioavailability. The absolute bioavailability for monkeys A–F are given in the table, below, following oral dosing of both formulas.

| Absolute Bioavailability of Rapamycin following Oral Dosing at 50 mg/kg | | |
|---|---|---|
| Monkey | Comparative Formula 4 | Formula I |
| A | NDL* | 9.19 |
| B | 0.57 | 7.37 |
| C | 8.82 | 14.8 |
| D | 2.55 | 7.14 |
| E | 0.79 | 2.78 |
| F | 5.64 | 5.84 |
| Average | 3.1 | 7.8 |

*NDL = no detectable levels

In addition to the abovementioned serum concentration tests, rapamycin formulations prepared as described above were tested for stability under refridgerated storage conditions (2° C.–8° C.). The table, below, indicates the concentrations of rapamycin, determined via HPLC analysis, in the initial formulations and following 9 months storage, as well as the percentage of the intial rapamycin concentration remaining at the end of the storage period (the values listed are within normal variables for this HPLC method of assay).

| Rapamycin Formulation Stability Assay Via HPLC | | | |
|---|---|---|---|
| Formulation | Initial Assay mg/ml | After 9 mos. mg/ml | After 9 mos. % of Initial Assay |
| Formula I | 48.85 | 49.6 | 101.5 |
| Comp. Formula 4 | 42.12 | 29.7 | 70.5 |

What is claimed:

1. A composition comprising, per 100 ml composition, from about 0.01 to about 10.0 grams of rapamycin, from about 0.1 to about 10.0 ml of surfactant, from about 0.1 to about 25 ml of N,N-dimethylacetamide, and from about 65 to about 99.8 ml of a 50% lecithin or phospholipid solution.

2. The composition of claim 1 which contains, per 100 ml composition, from about 0.05 to about 5.0 grams of rapamycin, from about 0.5 to about 8.0 ml of surfactant, from about 0.5 to about 20 ml of N,N-dimethylacetamide, and from about 72 to about 99.0 ml of a 50% lecithin or phospholipid solution.

3. A composition of claim 1 which contains, per 100 ml composition, from about 0.10 to about 1.0 grams of rapamycin, from about 1.0 to about 5.0 ml of surfactant, from about 1.0 to about 10 ml of N,N-dimethylacetamide, and from about 85 to about 98.0 ml of a 50% lecithin or phospholipid solution.

4. The composition of claim 1 which is contained within a starch capsule.

5. The composition of claim 1 which is contained within a gelatin capsule.

6. The composition of claim 1 which is dispersed in a liquid.

7. The composition of claim 6 in which the liquid is water.

8. The composition of claim 7 in which the composition of matter is dispersed in water at a concentration in the range of from about 1 part of the compositon of matter into about 9 parts water to about 1 part of the compositon of matter into about 499 parts water.

9. The composition of claim 1 wherein the surfactant is polysorbate 80.

10. A composition comprising, per 100 ml of the composition,
 a) a first 20 ml component of 2500 mg of rapamycin in N,N-dimethylacetamide; and
 b) a second component of from about 0.05 gm/ml to about 0.07 gm/ml of surfactant in lecithin, the second component being added to the first 20 ml component to complete a 100 ml composition volume.

* * * * *